(12) United States Patent
Ginot et al.

(10) Patent No.: US 8,129,113 B2
(45) Date of Patent: Mar. 6, 2012

(54) ANALYSIS CHIP WITH REFERENCE RANGE, KITS AND METHODS OF ANALYSIS

(75) Inventors: Frédéric Ginot, Saint Egrève (FR); Armelle Novelli-Rousseau, Seyssins (FR); Frédéric Mallard, Voreppe (FR); Florence Ricoul, Quaix-en-Chartreuse (FR)

(73) Assignee: Commissariat a l'Energie Atomique, Paris (FR)

( * ) Notice: Subject to any disclaimer, the term of this patent is extended or adjusted under 35 U.S.C. 154(b) by 499 days.

(21) Appl. No.: 10/584,916

(22) PCT Filed: Dec. 23, 2004

(86) PCT No.: PCT/FR2004/050757
§ 371 (c)(1),
(2), (4) Date: May 23, 2007

(87) PCT Pub. No.: WO2005/068654
PCT Pub. Date: Jul. 28, 2005

(65) Prior Publication Data
US 2008/0254448 A1      Oct. 16, 2008

(30) Foreign Application Priority Data
Dec. 29, 2003  (FR) ..................... 03 51222

(51) Int. Cl.
*C07H 21/04*   (2006.01)
*C12Q 1/68*    (2006.01)
*C12M 1/36*    (2006.01)
(52) U.S. Cl. ................... 435/6.1; 435/283.1; 435/287.2; 536/23.1

(58) Field of Classification Search ........................ None
See application file for complete search history.

(56) References Cited

U.S. PATENT DOCUMENTS
5,556,748 A * 9/1996 Douglas ........................... 435/6
(Continued)

FOREIGN PATENT DOCUMENTS
WO   WO 01/44506 A1   6/2001
(Continued)

OTHER PUBLICATIONS

Dolores J. Cahill et al., "Protein Arrays and Their Role in Proteomics," Adv. Biochem Engin/Biotechnol (2003) 83: 177-187.

(Continued)

*Primary Examiner* — Betty Forman
(74) *Attorney, Agent, or Firm* — McKenna Long & Aldridge LLP

(57) ABSTRACT

Analysis chip of at least one analyte, said chip comprising at least one analysis spot for recognition and immobilization specific to the analyte; and a reference range (G) comprising several reference spots each arranged on said chip in a defined manner and independently of one another, each reference spot of this range comprising, immobilized on its surface and in a defined proportion P that is different and known for each spot relative to the other reference spots of said range: a probe reference molecule (PRM) permitting recognition and hybridization specifically to a defined target reference molecule (TRM), and/or an inert oligonucleotide molecule (IM) incapable of recognition and hybridization with said PRM, these molecules both being unable to immobilize said analyte or analytes. The method of the invention comprises the use of said chip with its reference range for analysis of said, at least one, analyte.

13 Claims, 4 Drawing Sheets

U.S. PATENT DOCUMENTS

| | | | |
|---|---|---|---|
| 6,423,535 | B1 | 7/2002 | Arnold et al. |
| 6,537,801 | B1 | 3/2003 | Ida et al. |
| 6,884,582 | B1 | 4/2005 | Chaton et al. |
| 6,989,233 | B1 | 1/2006 | Vinet et al. |
| 2002/0102567 | A1 | 8/2002 | Fodor et al. |
| 2002/0110828 | A1* | 8/2002 | Ferea et al. ............ 435/6 |
| 2002/0187500 | A1 | 12/2002 | Laayoun |
| 2003/0143555 | A1 | 7/2003 | Bourget et al. |
| 2004/0016035 | A1* | 1/2004 | Floyd ............ D24/225 |
| 2004/0081967 | A1* | 4/2004 | Leproust et al. ............ 435/6 |
| 2005/0059068 | A1* | 3/2005 | Huang et al. ............ 435/6 |
| 2005/0142549 | A1 | 6/2005 | Ginot et al. |

FOREIGN PATENT DOCUMENTS

| | | | |
|---|---|---|---|
| WO | WO 01/44507 | A1 | 6/2001 |
| WO | WO 03/016550 | * | 2/2003 |
| WO | WO 03/016550 | A2 | 2/2003 |
| WO | WO 03/083127 | * | 10/2003 |
| WO | WO 03/083127 | A2 | 10/2003 |

OTHER PUBLICATIONS

Mary F. Lopez et al., "Protein micro- and macroarrays: digitizing the proteome," Journal of Chromatography B, 787 (2003) 19-27.

Sandra J. Rosenthal, "Bar-coding biomolecules with fluorescent nanocrystals," 2001 Nature Publishing Group, Jul. 2001, vol. 19, pp. 621-622.

A. Troesch et al., "Mycobacterium Species Identification and Rifampin Resistance Testing with High-Density DNA Probe Arrays," Journal of Clinical Microiology, Jan. 1999, pp. 49-55, vol. 37, No. 1.

Johannes Schuchhardt, et al., "Normalization Strategies for cDNA Microarrays," Nucleic Acids Research, 2000, vol. 28, No. 10, pp. E47I-E47V.

* cited by examiner

ANALYSIS CHIP WITH REFERENCE RANGE, KITS AND METHODS OF ANALYSIS

BACKGROUND OF THE INVENTION

1. Field of the Invention

The present invention relates to an analysis chip comprising a reference range, to a method of analysis of a sample using said chip, and to a diagnostic or analytical kit containing said chip.

The present invention is suitable for the qualitative and especially quantitative analysis of any analyte present in a sample.

The present invention is therefore positioned notably in the area of chemical or biological chips, for example DNA chips, protein chips, antibody chips, antigen chips, cell chips, receptor chips, or chips for other ligands known to a person skilled in the art and capable of specifically capturing and immobilizing one or more analytes.

Usually, applications using DNA chips are divided into two broad categories: gene expression (i) and genotyping (ii).

(i) Gene expression comprises using a DNA chip or chips for studying the variation of all or part of the transcriptome of a cell according to certain biological or physiological parameters: evolution of a cell during the development of an organism, carcinogenesis in a tissue, etc. It is becoming more and more evident that such expression profiles can also serve as diagnostic markers for multifactorial diseases, notably in oncology.

(ii) In applications of the genotyping type, the response required from the DNA chip is generally of the qualitative, yes/no type. In fact, we wish to know whether one or more particular sequence(s) is (are) present in the sample. When there is a great need for specificity, for example in the case of the detection of mutations, several oligonucleotides which only differ by one or two bases, are placed on the chip, and generally, a conclusion is made about the presence of the sequence corresponding to the strongest signal, e.g. of fluorescence.

The present invention is suitable for these two broad categories of applications and advantageously solves the many problems of the prior art that are described below, in particular in the carrying out of such studies and profiles.

Owing to its reference range, the chip of the present invention makes it possible to convert detection and/or analysis signals from a chip, for example from a biological chip, to an absolute, reproducible, stable unit that is comparable to other measurement results obtained from the same conversion.

2. Description of the Background Art

For the quantification of variations in gene expression, the biologist nearly always uses two samples which are hybridized simultaneously on a DNA chip: a reference sample, containing a certain mass of RNA or cDNA labelled with a first fluorochrome, for example fluorescein (read in the green), and a sample of interest for which measurement has to be carried out, containing the same mass of RNA or cDNA labelled with a second fluorochrome, for example Cy3 or Cy5 (read in the orange or the red). After hybridization, the DNA chip is read at the two wavelengths, and it is the ratio between the two intensities of the signals emitted which serves as the signal.

It is therefore a question of a relative measurement with internal reference in each experiment. This method works well, but is quite laborious in use, and there are certain pitfalls, such as bias in labelling according to the sequences, or a deviation in reading that varies depending on the wavelength.

Another technique of quantification is used for the gene expression chips developed by the company Affymetrix. In this method, each sequence placed on the chip is represented by a set of oligonucleotides, and each oligonucleotide is in the form of two oligonucleotides, the one perfectly complementary to the required sequence, the other having a point mutation ("mismatch"). The sample of interest is then hybridized on the chip, a single color being used. The complementary-mismatch difference is then used as primary signal, these signals being averaged over the set of oligonucleotides representing a gene. Moreover, a "reference gene" is arranged on the chip by the same technique; this reference gene, taken from the so-called housekeeping genes of the organism, is assumed to maintain constant expression regardless of the physiological conditions of the cell. Then the "primary signal" of each gene is divided by that of the reference gene, for example to avoid the variations in brightness of the fluorescence due to the surroundings. It is then possible for different experiments to be compared with each other.

This technique has the advantage of being monochrome, and therefore does not have the aforementioned drawbacks with the two markers. However, it necessarily uses short oligonucleotides (20 to 25 bases), and therefore there are other pitfalls, since some genes occur in various forms (alternative splicing). This method therefore requires more spots on the DNA chip and more knowledge about the various forms of the RNAs of the genes represented on the chip than with the other methods of the prior art. Moreover, the results vary depending on the choice of reference gene, even when the latter is selected very carefully. Therefore the results cannot always be compared.

The aforementioned methods, provided certain controls and some repetitions of the experiments are employed, can be relatively reliable and therefore offer a research tool that can be used by biologists. However, it must be noted that the measurements are relative, since the signal is a dimensionless number resulting from the ratio between two measurements with units that are generally arbitrary (arbitrary units of fluorescence). Therefore it is not possible to compare experiments performed with different reference samples for example, without additional testing. Moreover, as the measurements are in arbitrary units, it is also rather difficult to know what causes the problems in the case of low intensities: it is difficult to know whether it is an instrumental problem, a problem connected with the chip itself, with the sample, with the operating procedure, or with the result of the experiment.

In applications of the genotyping type, the response required from the DNA chip is generally of the qualitative, yes/no type, as explained above. Furthermore, with the chips of the prior art, the results are relative, since the intensities of different oligonucleotides under investigation on one and the same chip are being compared.

However, for certain applications, such as the detection of mixtures of several sequences, it would be advantageous to be able to compare the signals between several experiments, which is impossible at present with the chips currently available; it is constantly necessary to repeat one or more experiments to obtain relative measurements from which conclusions can be drawn, which is time-consuming and expensive.

Moreover, in routine diagnosis, the problem of quantification of the results can be solved with a calibration curve. A reference sample is diluted in a predetermined manner at various concentrations in a suitable diluent, and the biological test is performed for each dilution away from the chip. This provides a reference curve. When a real biological test is carried out, the result in arbitrary unit is plotted on the reference curve, and the concentration of analyte in the sample is deduced from this. However, it is important for the test to be performed with exactly the same elements as those used for constructing the reference curve. Moreover, in tests with enzymatic development for reading, for example ELISA, ELOSA, etc., a reference curve is also required for each manufacturing batch of the tests. Moreover, additional calibration points for resetting the reference curve for each user must be performed for correcting variations from one machine to another, from one temperature to another, from one laboratory to another, for possible aging of the reagents, etc. These additional calibration tests must be repeated regularly by the users, for example every week.

This method of quantification, although usual, is therefore complicated and expensive. Moreover, it is not easily applicable to DNA chips; in fact, it would be necessary to use a DNA chip for each point of the reference range, and keep repeating the experiment (at each change of batch of marker, or at regular intervals, for example every month, to check for possible drift of the instrumentation), which is too expensive for the laboratories.

Therefore there is a real need for a chip and a method of analysis which enable the many aforementioned problems of the prior art to be solved, and notably which are reliable, accurate, and reproducible; which can be applied to the various known and future DNA chips; which make it possible to compare the signals between several experiments; which make it possible to avoid using a DNA chip for each point of the reference range; and which make it possible to avoid constantly repeating the calibration test (at each change of batch of marker, or at regular intervals, for example every month, and to check for possible drift of the instrumentation), so as to reduce the complexity and costs of analyses on chips, for example on biological chips, for the laboratories, in industry and in research.

In the following description, the references in square brackets [ ] refer to the list of references given after the examples of application of the invention described below.

SUMMARY OF THE INVENTION

The present invention meets precisely this need and solves the many aforementioned problems of the prior art, and others, notably in that it provides an analysis chip, as well as a method of analysis using this chip, as defined below.

The analysis chip of the present invention is an analysis chip for at least one analyte present in a liquid sample, said chip comprising:

a) at least one analysis spot of said, at least one, analyte, said analysis spot being arranged on the chip to permit the recognition and specific immobilization of the analyte; and b) a reference range (G), said reference range being constituted of several reference spots each arranged on said chip in a defined manner, and independently of one another, each reference spot of this range comprising, immobilized on its surface and in a defined proportion P that is different for each spot relative to the other reference spots of said range: (i) at least one probe reference molecule (PRM) permitting the recognition and specific binding to a defined target reference molecule (TRM), and/or (ii) at least one inert molecule (IM) incapable of recognizing and binding to said target reference molecule, the probe reference molecule and the inert molecule both being incapable of recognizing and immobilizing said analyte(s); with $$P = \frac{\text{number of } PRM}{\text{number of } PRM + \text{number of } IM} \text{ and } 0 \le P \le 1$$

the sum of the number of PRMs+number of IMs being constant from one reference spot to another.

The method of analysis of the present invention is a method of analysis in vitro of at least one analyte that may be present in a liquid sample comprising the following steps:

(A) optionally, immobilization of a first detecting means on the analyte;

(B) addition, to the sample to be analyzed, comprising the optionally labelled analyte, of a target reference molecule (TRM) on which a second detecting means, identical to or different from the first detecting means, has optionally been immobilized, said TRM being capable of recognizing and of binding specifically to the probe reference molecule (PRM) of an analysis chip according to the invention, said TRM being added to said sample in a sufficient amount to saturate the PRM of the reference range (G) of said chip, thus creating a reference range that is a function of the defined proportion P which is different for each reference spot;

(C) bringing the sample to be analyzed comprising the TRM into contact with said analysis chip comprising at least one analysis spot of said at least one analyte in physicochemical conditions such that: on the one hand, the analyte to be analyzed, if it is present, binds to its analysis spot on the chip; and on the other hand, the TRM specifically recognizes the PRM and binds to the latter on the various reference spots of the reference range of the chip;

(D) determination of a reference signal emitted, if applicable owing to the second detecting means, by each reference spot of the reference range, said signal being a function of the amount of target reference molecule immobilized on the latter; and (E) determination of an analysis signal emitted, if applicable owing to the first detecting means, by said, at least one, analysis spot and being a function of the amount of analyte immobilized by the analysis spot, and comparison with the signals determined in Step (D) for expressing this analysis signal as a function of P.

The term "analyte" means all or part of the particle or molecule that we wish to analyze, i.e. detect and/or quantify, for example a microorganism, a bacterium, a fungus, a virus, a eukaryotic cell, a cell such as a tumor cell, a chemical compound or molecule, a molecule such as a peptide, a protein, a glycoprotein, a lipoprotein, an enzyme, a polysaccharide, a lipid, a glycolipid, a lipopolysaccharide, a ribonucleic acid (RNA), a deoxyribonucleic acid (DNA), a hormone, an antigen, an antibody, a growth factor, a hapten, etc.

The sample can be a solution, a cellular extract, or a sample obtained from an animal or vegetable organism. This sample can be diluted, if necessary, for use in the present invention. A person skilled in the art will be familiar with the handling of such samples and their dissolution and/or their dilution, their purification and/or their concentration, for analysis on an analysis chip, for example a biological or chemical chip. These same manipulations are employed for carrying out the present invention.

The chip of the present invention comprises, in combination, on the one hand, at least one analysis spot of at least one analyte to be analyzed, and on the other hand, a reference range, both arranged on the surface of one and the same chip according to the present invention.

The chip of the present invention is constituted in the same way as the analysis chips of the prior art, except that it additionally comprises a reference range in the sense of the present invention. The steps of production of the reference range are therefore added to those of fabrication of the chip. DNA chips that can be used for carrying out the present invention and their method(s) of production are described for example in document [1] of the bibliography. Protein chips that can be used for carrying out the present invention and their method(s) of production are described for example in documents [2] and [3] of the bibliography.

The chip of the present invention therefore has a very wide range of uses as an analysis tool. Thus, by "analysis" we mean "qualitative analysis" of a sample, i.e. detection of analyte(s) present in a sample and/or "quantitative analysis", i.e. quantitative determination of analyte(s) present in a sample. Some examples are given below.

According to the invention, the "spots" comprise means for recognizing and immobilizing, exclusively and specifically, either "the analyte" (analysis spot) or "the target reference molecule" (spot of the reference range).

For the "analysis spot", these means comprise the probe molecules specific to said analyte. The specific probe molecule can be for example a molecule of DNA or of RNA permitting recognition and immobilization of a complementary analyte (DNA or RNA) by hybridization; of an antigen or of an antibody recognizing and immobilizing the analyte by an interaction of the antigen/antibody type; of a protein recognizing and immobilizing the analyte by an interaction of the protein/protein type; of an enzyme or of a substrate recognizing and immobilizing the analyte by an interaction of the enzyme/substrate type; etc.

For example, when the analyte is a nucleic acid, the, at least one, analysis spot is a spot functionalized by a nucleic acid complementary to the latter. For example, when the analyte is an antibody or an antigen, the, at least one, analysis spot is a spot functionalized respectively by an antigen or an antibody.

The methods of production of these analysis spots and their functionalization are known to a person skilled in the art and are disclosed for example in the aforementioned documents. Functionalization of the analysis spots of the chip can be effected for example by means of a robot for dispensing drops of a functionalization solution, for example a robot of the Packard Instrument® or GeSim Type®.

The chip of the present invention can comprise several analysis spots, which may be identical or different, in the same way as the analysis chips currently used in the laboratory.

The reference range of the present invention is constituted of reference spots, which are also spots for recognition and immobilization of a target, but these reference spots are characterized in that they cannot recognize and immobilize the analyte or analytes to be analyzed, but only a defined target reference molecule. The reference spots of this reference range are as defined above in points (i) and (ii) of the method of the invention.

According to the invention, the probe reference molecule, the target reference molecule, and the inert molecule are selected together and as a function of the analyte for which the chip of the present invention is intended, so that they have least possible interaction with the analyte.

According to the invention, preferably, the target reference molecule is of the same nature as the analyte. It can also be of a different nature. The main point is that the target reference molecule should neither be recognized nor immobilized by said, at least one, analysis spot.

According to the invention, the probe reference molecule is selected for specifically recognizing and immobilizing said target reference molecule. Preferably, this probe reference molecule is of the same nature as the probe molecule that is specific to the analyte. It can also be of a different nature. The main point is that the probe reference molecule neither recognizes nor immobilizes the analyte.

For example, according to the invention, the target reference molecule and the probe reference molecule can be, for example, complementary oligonucleotides (DNA or RNA) for recognition and immobilization of the target reference molecule by hybridization on the spots of the reference range comprising the probe molecule; for example an antigen and its specific antibody permit the target reference molecule to be recognized and immobilized by an interaction of the antigen/antibody type on the spots of the reference range comprising the probe molecule; for example proteins permitting the reference target to be recognized and immobilized by an interaction of the protein/protein type on the spots of the reference range comprising the probe molecule; etc.

According to the invention, the at least one analyte and the target reference molecule are preferably oligonucleotides or antibodies. The functionalization of the various spots (analysis and reference range) on a chip according to the present invention using probe and/or inert oligonucleotides or antibodies or antigens can be carried out using the techniques of functionalization with which a person skilled in the art is perfectly familiar in the field of chips with oligonucleotides or antibodies or antigens. Techniques that can be used are described for example in the aforementioned documents.

According to the invention, the inert molecule of the reference range, also called "non-specific" molecule, is selected in such a way that it neither recognizes nor immobilizes the target reference molecule and the analyte or analytes. Preferably, according to the invention, the inert molecule is of the same nature as the probe reference molecule. In fact, this means it is not necessary to take into account the non-specific interactions that might interfere with the analysis, while using the chip of the present invention, for example between the inert molecule and the analyte or analytes on the one hand and the target reference molecule on the other hand, and obtain a reliable reference range. In the preceding examples, the inert molecule of the reference range can therefore be respectively a DNA or an RNA, an antigen or an antibody, a protein, an enzyme or a substrate. The reference inert molecule is also immobilized on the spots of the reference range according to the techniques of chip functionalization known to a person skilled in the art, for example those described in the aforementioned documents.

According to the invention, preferably the probe reference molecule, the target reference molecule and the inert molecule are oligonucleotides. The production of oligonucleotide sequences, for example artificial, meeting the definitions of the probe and target reference molecules and of the inert molecule of the present invention, and functionalization of spots on a chip using these probe and inert oligonucleotides for the production of the reference range is in fact facilitated and uses the techniques with which a person skilled in the art is perfectly familiar in the field of oligonucleotide chips.

In-situ systems: certain methods of production of DNA chips employ in-situ synthesis of the oligonucleotides (for example the methods of production of the GeneChip chips of the company Affymetrix®, or the chips of the company Agilent). In these methods, each oligonucleotide is synthesized in situ on the chip. The three-dimensional addressing of the monomers to be coupled is effected either at the level of deprotection in a conventional cycle of synthesis of oligonucleotides (photo-deprotection for Affymetrix); or at the level of coupling of the monomers ("spotting" for Agilent). Such a technique of in-situ synthesis makes it possible to produce the analysis spots of the chip of the present invention, and, by adding as many cycles of synthesis as there are points in the reference range, and in these cycles of synthesis, by directly coupling the mixture of probe reference oligonucleotide/inert (non-specific) oligonucleotide at a suitable place on the substrate forming the chip (instead of only coupling one monomer), a reference range according to the invention is produced.

According to the invention, the reference range is constituted of several reference spots arranged on said chip in a defined manner and independent of one another. In fact, for the reference range to be usable, it is necessary for each reference spot to be distinct from the other reference spots so that the various spots in this range supply signals that are independent and can be utilized for the analysis when using the chip.

Each spot of the reference range is distinguished from the other spots of this range by its defined proportion P as defined above: the amount of probe reference molecules relative to the inert molecules is therefore known for each reference spot. This defined proportion P is obtained on each reference spot by functionalizing each spot, independently of the others, by means of a solution with a defined concentration of probe reference molecule and/or inert molecule. According to the invention this proportion P can range from 0, in the case when the reference spot only contains the inert molecule, to 1, in the case when the reference spot only contains the probe reference molecule. The main thing is that the total amount of probe reference molecule and inert molecule (PRM+IM) should be equal from one spot to another, for the reference range to be accurate.

Preferably, in the example where the reference probe and inert molecules are oligonucleotides, they are selected in such a way that they have equal effectiveness of attachment to the spots of the reference range during fabrication of the chip. Thus, after attachment, the proportion of reference oligonucleotide is equal to that of the initial dilution. This makes it possible to pass advantageously from the unit "% of dilution" to the unit "% of reference oligonucleotides attached" in the course of an analysis using the chip of the present invention.

In the example of oligonucleotide chips according to the present invention, in contrast to the cDNA chips or PCR product chips, preferably, the total amount "reference probe oligonucleotides+non-specific inert oligonucleotides" is equivalent to the amount of probe oligonucleotides used for each analysis spot for the fabrication of the chip. Oligonucleotides of the same length will also preferably be used. Thus, as the efficiency of attachment has little dependence on the sequence, for each spot, it is possible to express the signal in "percentage of spots hybridized", 100% corresponding to saturation of the surface.

Preferably, the spots of the reference range are disposed on the chip linearly and are arranged in relation to the proportion P of each spot, for example from the spot with the highest concentration to the spot with the lowest concentration of probe reference molecule. In fact this gives a calibration scale that can be utilized more easily when using the chip. The increase in the proportion P from one reference spot to another close to it in such a range can be linear, for example, in percentage of probe reference molecule on successive different spots, of 0%; 20%; 40%; 60%; 80% and 100%, or nonlinear, for example 0%, 5%, 10%, 20%, 50%, 100% or even 0%; 0.1%; 1%; 10% and 100%. There is no other restriction on application of the present invention than that of being able to assign clearly, to a signal supplied from a spot of the reference range, a defined proportion of probe reference molecule.

The number of reference spots of the reference range is determined as a function of the required accuracy of analysis and of the dynamic range of the test when using the chip. For example, three reference spots for example with, successively, 0%, 50% and 100% of probe reference molecule only provide three calibration results as a basis for the results of analysis of the analyte, whereas five reference spots for example with, successively, 0%, 20%, 40%, 60%, 80% and 100% of probe reference molecule provide six calibration results, giving a more accurate reading of the results of analysis. For example, the reference range can comprise from 1 to 50 reference spots, for example from 2 to 20. A person skilled in the art will easily determine, depending on the required accuracy of analysis and the dynamic range of the concentrations, the number of different reference spots required and their arrangement or disposition on the chip.

The appended FIG. 1 shows schematically, in cross section, a reference range (G) on a chip (C) according to the present invention. This diagram shows various reference spots (1a, 1b, 1c and 1d), on which the probe reference molecules (PRM) (shown as thick lines) and the inert molecules (IM) (shown as thin lines) are immobilized. The analysis spots are not shown. The left-most spot only contains PRM (100%), and the right-most spot only contains IM (0% PRM). The intermediate spots contain intermediate proportions of PRM. The sum PRM+IM is constant from one spot to another.

According to the invention, several reference ranges, which may be identical or different, can be arranged on one and the same chip. The use of several reference ranges, although not obligatory, can in some cases improve the accuracy of the analyses performed. This may be so for example when the sample comprises several analytes to be analyzed simultaneously on the chip, by an oligonucleotide and an antibody. A person skilled in the art will easily determine, depending on the analysis for which the chip is intended, the most appropriate implementation.

The full importance of the present invention becomes clear when the chip having this reference range is used for the analysis of a sample comprising or likely to comprise one or more analytes to be analyzed, notably in the method of the invention.

In the method of the invention, the analyte and the target reference molecule are preferably of the same nature, without being limited to this embodiment. Also preferably, the analyte and the target reference molecule are oligonucleotides or antibodies, without being limited to this embodiment. In a particularly advantageous embodiment of the invention, the probe reference molecule, the target reference molecule and the inert molecule are oligonucleotides for the same reasons as those presented above.

Similarly, and for the same reasons as those presented above, the, at least one, analyte is advantageously a nucleic acid, and the analysis spot of said analyte on the chip is a spot functionalized by a nucleic acid complementary to the latter. The analyte can also be an antigen or an antibody, and the analysis spot of said analyte on the chip can be a spot functionalized respectively by an antibody or an antigen recognizing and immobilizing the latter.

Step (A) of the method of the invention is optional. In this Step, a first detecting means can be immobilized on the analyte. It can be any means known to a person skilled in the art that can be used for detecting an analyte immobilized on a specific probe molecule (probe/analyte combination) immobilized on a chip. This means can involve for example a first marker, which can be immobilized either on the specific probe molecule, or on the analyte. This means can also be another molecule for indirect labelling, for example a biotin, depending on the labelling technique employed. The markers and the labelling techniques that can be used for carrying out the present invention are, without limitation, those known to a person skilled in the art in the field of analysis chips, for example biological chips, for example DNA or RNA chips, antibody/antigen chips or chips using an enzyme/substrate interaction.

The markers that can be used can be selected for example from the group comprising fluorescent markers; radioactive markers; standard, colored or fluorescent latex particles; photonic crystals (also called "quantum dots"); colloidal gold; and enzymatic markers. Among the fluorescent markers, we may mention fluorescein, Cy3, Cy5 and rhodamine. Among the radioactive markers, we may mention for example $^{32}P$, $^{33}P$, $^{35}S$, $^{125}I$ and $^{3}H$. Among the enzymatic markers, we may mention alkaline phosphatase, horse radish peroxidase (HRP), β-galactosidase, acetylcholinesterase. For these enzymes, there are colored, fluorescent or luminescent markers. In this case, they are molecules transformed by the enzyme, which, after transformation, become colored (or the absorption wavelength changes), fluorescent, luminescent or redox. The enzymatic markers that are used routinely in diagnostic immunoanalyses can also be used. These fluorescent or enzymatic markers, and others, that can be used in the present invention, are available for example from the catalogues of the companies Sigma/Aldrich, Molecular Probes, Amersham Pharmacia Biotech., Stratagene, etc. Documents [4] and [5] of the bibliography describe methods of using these markers that can be used for carrying out the present invention. Markers in the form of particles that can be used in the present invention are available from several suppliers, for example Molecular Probe, Miltenyi, Estapor/Merck, Polymer Solutions, etc. Document [6] of the bibliography describes methods employing these markers in the form of latex or colloidal particles that can be used for carrying out the present invention. For the use of photonic crystals it will be possible to use for example the method described in document [7] of the bibliography.

For certain markers, especially the enzymatic markers, the detectable product may move some distance away from the spot where it was produced, by molecular diffusion, and contaminate neighboring spots. This can cause a disturbance in the use both of the reference range and of the signals emitted by the spots for recognition of the analyte or analytes. That is why the inventors prefer luminescent markers, as there is limited diffusion: once the enzymatic product has emitted a photon, it cannot emit any more. To avoid the phenomenon of diffusion, it is also possible to use so-called precipitating enzymatic substrates: the enzymatic product is insoluble, and is precipitated in situ, i.e. on the spot. For example, tetramethylbenzidine (TMB) can be used for the HRP enzyme, and the combination of Nitroblue Tetrazolium with 5-bromo-4-chloro-indolyl phosphate (NBT+BCIP) for alkaline phosphatase.

According to the invention, in order to avoid these phenomena of diffusion which can interfere with the reading of the chip with certain markers, but also, in general, to avoid any phenomenon of diffusion between adjacent spots, the inventors recommend the use of chips on which the spots (for recognition and immobilization of the analyte and/or of the reference range) are provided with means for ensuring that droplets of the sample obtained in Step (B) are formed exclusively on each of the spots, without these droplets being able to diffuse between them. These means can be for example in the form of a boundary, for example of resin, surrounding each spot. These means can also be in the form of a ring around each spot and displaying much greater wettability for the sample than the rest of the chip surface, so that a droplet of sample is retained by each ring exclusively on each spot. This ring can be for example a ring of black silicon obtained by microgravure on a silica surface or an electrode for capturing a droplet of sample by electro-wetting. Regardless of the means employed for formation of droplets, the chip surface is preferably non-wetting with respect to the sample. The chip of the present invention can therefore advantageously be provided with these means in order to increase the quality or the reliability of the measurements obtained.

In Step (B), the target reference molecule on which a second detecting means identical to or different from the first detecting means is optionally immobilized, is added to the sample, as defined above. This second means can involve for example a second marker, which can be immobilized on the target reference molecule or on the probe reference molecule. It can also involve a molecule other than a marker, but which is employed in a method of indirect labelling (for example biotin). This marker can be selected for example from those mentioned above. The second detecting means is preferably, but not necessarily, identical to the first detecting means. The main thing is that the immobilization of the target reference molecule on the probe reference molecule of the reference range can be detected on the chip by a detectable signal.

According to the invention, the analyte alone may be labelled, or only the target reference molecule, or both, or neither of the two. In fact, some methods of detection are able to detect molecular interaction (probe/target immobilization on a chip) without a marker. Some examples are given below.

The target reference molecule on which the second detecting means is optionally immobilized is added to the sample in sufficient quantity so that the maximum number of probe molecules of the spots of the reference range recognize and immobilize the target molecule in the experimental conditions used for bringing the sample into contact with the chip (Step (C)). Addition to the sample can be carried out by, preferably homogeneous, mixing with the sample.

In Step (C), the mixture from Step (B) is brought into contact with the chip of the present invention, in the physicochemical conditions defined above. These conditions are known to a person skilled in the art in the field of analysis chips, for example biological chips, for example DNA chips, RNA chips, antibody/antigen chips, protein chips, etc. These are, for example for the aforementioned chips, the conditions of pH, temperature and ionic strength permitting the recognition and immobilization of the analyte or analytes (DNA, RNA, antibody, antigen, protein, etc.) on their recognition spot or spots, and of the target reference molecule (DNA, RNA, antibody, antigen, protein, etc.) on the spots of the reference range comprising the probe reference molecule. The advantage of the present invention is that the recognition and immobilization of the analyte by the, at least one, analysis spot and the formation of the reference range by the immobilization of the probe reference molecule on the reference spots are effected simultaneously and in the same operating conditions. The effect is obvious: the signals emitted by the reference range have been obtained in the same operating conditions as were used for immobilizing the analyte. The results of analysis are therefore more reliable than those obtained by the methods of the prior art.

In general, the analysis spots and the spots of the reference range can be brought into contact with the sample by the usual means of the technology of analysis chips used for the distribution of a sample on functionalized zones.

On a chip comprising means for limiting the formation of droplets of the sample on the spots of the chip, this bringing into contact can be effected very simply by covering the spots with the sample, then withdrawing the sample so as only to leave the droplets of sample captured by these means on the analysis spots and the spots of the reference range of the chip.

The appended FIG. 2 shows schematically, in cross section, the reference range (G) of FIG. 1 after the step of bringing into contact. This diagram shows the target reference molecules (TRM) immobilized on the probe reference molecules (PRM). The TRM are labelled by means of a marker (Mq). It is clear that the left-most spot (100% PRM) will give the strongest signal from the marker, and the right-most spot (0% PRM) will not give a signal. Intermediate signals will appear on the spots in the middle.

As with the use of the analysis chips known to a person skilled in the art, this Step (C) can be followed by step(s) of washing and rinsing in physicochemical conditions which do not disrupt the immobilization of the analyte on its analysis spot, as well as the immobilization of the target reference molecule on the probe reference molecule. These steps of washing and rinsing are known to a person skilled in the art and can be found in the aforementioned documents. They make it possible to remove the excess of reagents and molecules that are not immobilized on the chip.

In Step (D) of the method of the invention, a signal emitted by each spot of the reference range, reflecting the amount of immobilization of target reference molecule immobilized on each spot of the reference range, is determined. In Step (E) of the method of the invention, notably a signal emitted by each analysis spot, reflecting the amount of analyte immobilized on each analysis spot, is determined.

These determinations can be performed in various ways depending on whether or not markers are used in the method of the invention. The main thing is to be able to assign a definite signal representative of the amount of targets immobilized on each of the spots of the reference range, and a definite signal representative of the amount of analyte immobilized on each analysis spot.

When markers are used, the technical means that are appropriate for the detection of these markers are used. If the first and second detecting means used employ the same markers, the detecting means will be the same for the various analysis spots and for the various spots of the reference range. These techniques of signal reading are known to a person skilled in the art. In the aforementioned examples of markers, they make it possible to detect for example an amount of fluorescence, an amount of radioactivity, an amount of enzymatic reaction product, luminescence, etc. The aforementioned documents relating to markers present techniques for determination of these signals which can be used for implementing the method of the invention.

According to the invention, the signal from each spot of the reference range and/or from each analysis spot can also be determined, especially if markers are not used, by a method selected from the group comprising the methods of detection by surface plasmon resonance, methods of photothermal detection, ellipsometric methods, methods of photometric detection and methods of acoustic detection. These methods are known to a person skilled in the art. Documents [8] and [9] of the bibliography disclose methods of photothermal detection that can be used for carrying out the method of the present invention for detecting a signal without a marker.

According to the invention, it is possible to use different methods of determination of the signals, with or without markers, for the analysis spot and for the reference range. Thus, the method of the invention makes it possible to compare the results obtained with a method without labelling (analysis spot or reference range) with other results obtained on the same chip with labelling (analysis spot or reference range), for example by fluorescence. The main thing is that the operating conditions of immobilization of the analyte on its analysis spot and of the target reference molecule on the reference range should be effected simultaneously on the same chip and in the same operating conditions.

In Step (E), the signal emitted by each analysis spot is compared with the various signals emitted by the reference range for expressing said signal of the analysis spot as a function of the proportion P defined above. In fact, the intensity of the signal emitted by each analysis spot is compared with the various signals of the reference range for deducing from that, relative to an equivalent signal of the reference range, a signal value relative to the proportion P. Other comparisons which take account of other criteria of the reference range are also possible (IM number, PRM number, IM/PRM ratio, PRM/IM ratio, etc.)

Advantageously, if the nature of the analyte and of the reference probe is the same, the proportion of analyte(s) on each analysis spot can be determined directly, reliably and reproducibly, by simple reading. In fact, on the basis of the present invention this determination is carried out by means of a reference range performed simultaneously, from the same sample, and therefore in the same operating conditions, as for the analyte.

If the nature of the analyte is different from that of the probe reference molecule, it is possible to determine a relative value, which however has the advantage of being stable, reproducible, and of integrating the operating conditions of the analysis with those which permitted the simultaneous formation of the reference range, on the same chip, from the same sample. This relative value is therefore more reliable than those obtained by the methods of the prior art.

In a particular example of application of the present invention, when the analyte, the probe molecules specific to the analyte, the probe reference molecules, reference targets and inert targets are oligonucleotides, Step (C) of bringing into contact is for the purpose of on-chip hybridization of the analyte with the probe reference molecule, and hybridization of the target reference molecule with the probe reference molecule. For this hybridization, a target reference oligonucleotide containing the sequence complementary to the probe reference oligonucleotide of the reference range, and labelled preferably, but not necessarily, in the same way as the analyte, is added to the sample containing the analyte. This oligonucleotide is used in slight excess, in such a way that all the probe reference molecules of the spot of the reference range comprising 100% of reference oligonucleotide are hybridized in the experimental conditions of hybridization used. Thus, for each spot of the reference range, all the spots that can be hybridized will be hybridized. It will then be possible to express the signal from each analysis spot of the DNA chip in "% of reference dilution". By using, in different analyses, the same reference oligonucleotides and non-specific oligonucleotides (i.e. not recognizing and not immobilizing the analyte), this unit is independent of the sample, of the labelling chemistry, of the marker used (green, red or blue, fluorescent, photonic, etc.), of the conditions of hybridization (provided that the hybridization of the reference oligonucleotide is complete), of the chip batch, of the efficiency of attachment, etc., enabling the experiments to be compared directly with one another, without additional experiments as was necessary in the methods of the prior art.

Generally speaking, it is possible to perform a direct reading, or construct, from the reference range, a reference curve, for example (signal determined)=f(P), which can be used for analysis of the analysis spots of said chip.

The chip and the method of the present invention are therefore reliable, accurate, and the results are reproducible. The present invention applies to the various known and future DNA chips; it makes it possible to compare the signals between several experiments, avoids using a DNA chip for each point of the reference range, and avoids the constant repetition of the calibration experiments as is necessary with the methods of the prior art.

Advantageously, in the case of the methods of detection with enzymatic labelling, for example luminescence, the present invention makes it possible to avoid having to calibrate the activity of each batch of enzyme, at the manufacturer and at the customer. This therefore represents a considerable simplification of the "chain of metrology".

The present invention therefore reduces the complexity and the costs of on-chip analyses, for example on a biological chip, for the laboratories, in industry and in research.

Since the present invention can be based on all the analysis chips of the prior art employing spots for recognition and immobilization of an analyte, a person skilled in the art will readily understand that it will find application in all fields where this type of chip can be used.

Thus, the present invention also relates to a diagnostic kit comprising a chip according to the invention. In this case, the analysis spots of the chip of the present invention comprise the probe molecules specific to recognition of the analyte required for obtaining the results which it will then be possible to interpret for establishing a diagnosis. For example, it can be a question of probe molecules selected from oligonucleotides, cDNA, antibodies, lectins, aptamers, etc.

The present invention also relates to an analysis kit comprising a chip according to the invention. In this case, the analysis spots of the chip of the present invention comprise the probe molecules specific to recognition of the analyte required in order to carry out said analysis. It can be a kit for qualitative or quantitative analysis. For example, it can be a question of probe molecules selected from oligonucleotides, cDNA, antibodies, lectins, aptamers, etc.

The present invention also relates to the use of a chip according to the present invention for monitoring variations in gene expression in tissue cells in vitro. For example document [1] describes a protocol that can be used on the chip of the present invention for monitoring these variations in gene expression.

The present invention also relates to the use of a chip according to the invention in a method of genotyping in vitro. For example document [1] describes a protocol that can be used on the chip of the present invention for carrying out a method of genotyping.

For example, concerning the usefulness and for the use of the gene expression chips according to the present invention, reference may be made to the description given in document [10] which describes protocols that can be used for carrying out the method of the invention in these applications.

For example, regarding the use of the present invention in a method of genotyping, for example for diagnostic purposes, reference may be made to documents [11] and [12] each of which describes protocols that can be used for carrying out the method of the invention in this application.

Other characteristics and advantages will become clear on reading the following examples, given for purposes of illustration, referring to the appended drawings.

EXAMPLES

Example 1

Chip According to the Present Invention 1.1 Chip Substrate

The substrate used for fabrication of a chip according to the invention is a monochrome imager of the type "VV5501 VGA Monochrome Image Sensor"® of ST Microelectronics) the main technical characteristics of which are shown in the following table:

| Image format | 640 × 480 pixels (VGA) |
| Pixel size | 5.6 μm × 5.6 μm |

Figure 6:
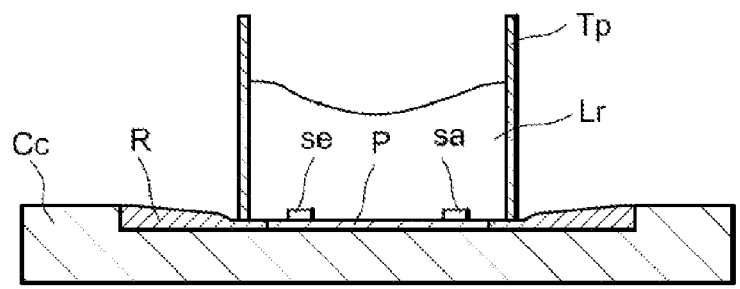
FIG. 6 is a schematic representation of the setup used by the present inventors for the fabrication of chips according to the present invention.
Figure 8:
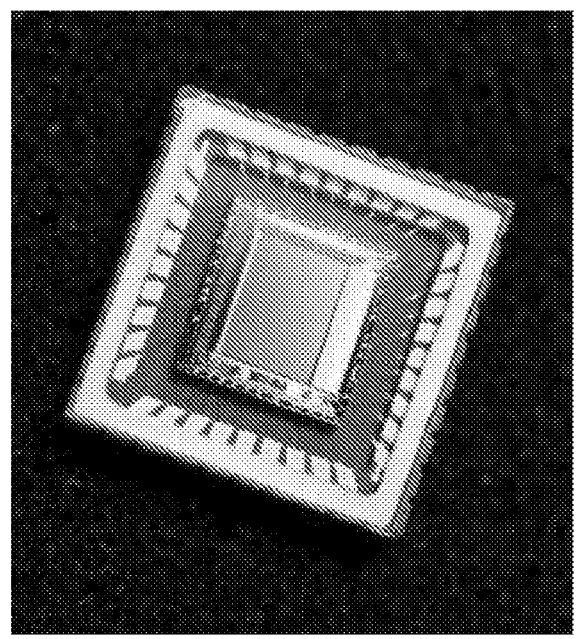
FIG. 8 is a photograph of a chip substrate used for fabrication of a chip according to the present invention.

A top view of this substrate is shown in the photograph in FIG. 8. It has a silicon surface at its centre. FIG. 6, described below, is a schematic cross section of this chip which also has a plastic tube glued on top (see below).

This substrate is in fact intended for the manufacture of a low-cost digital camera with gain and exposure control functions and theoretically has a signal to noise ratio of 56 dB. Moreover, it only requires very few external components for its operation and is provided with a kit (software and hardware) for management of the internal parameters of the camera.

1.2 First Steps in Fabrication of the Chip

Figure 1:
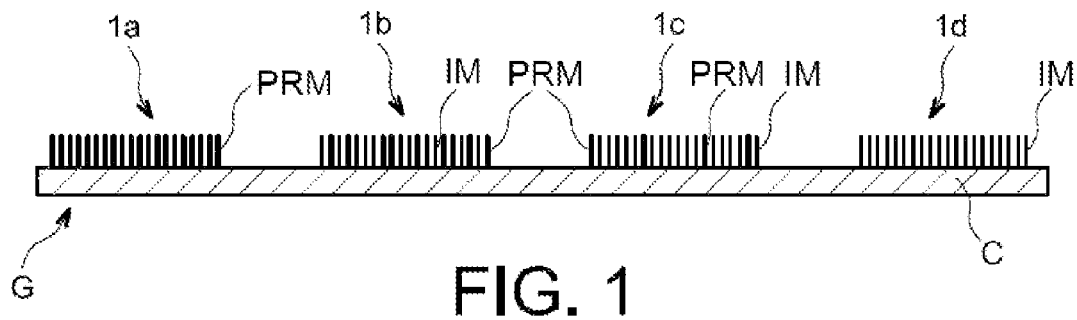
FIG. 1 is a schematic representation of a reference range on a chip according to the present invention.
Figure 2:
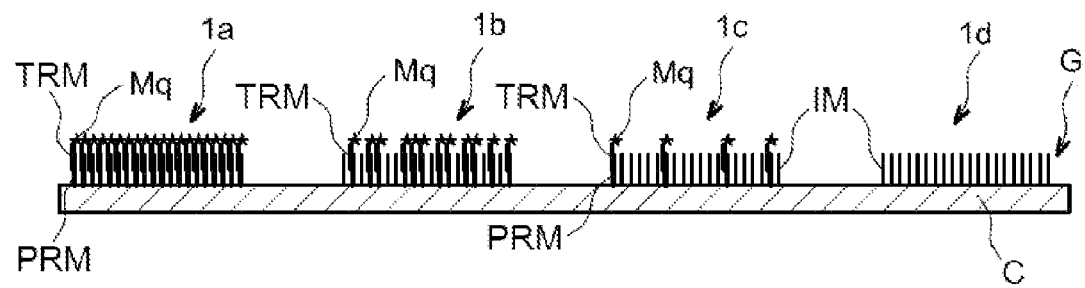
FIG. 2 is a schematic representation of a reference range on a chip according to the present invention when the target reference molecules are immobilized on the probe reference molecules. Markers are also shown.

Chip substrates as described in the preceding paragraph 1.1 were modified for functionalizing the silicon surface (see FIG. 1). To gain access to the silicon surface of the photodetector (at the centre of the substrate), the glass cover was removed and the bonding connections were buried under globtop resin (a general term denoting any resin used for protecting the bonding connections). The passivation layer (silicon nitride) at the centre of the photodetector was functionalized (silanization+attachment of the spot capture probes).

For the subsequent experiments of functionalization of the silicon surface, a plastic tube was glued (UV adhesive) on the chip to define a reaction chamber above the active surface, in which the hybridizations, washings, and development were carried out. FIG. 6 is a schematic representation of the setup used: it comprises a resin (R) for protecting the connections of the chip, the silicon surface (P), a ceramic frame (Cc), the glued plastic tube (Tp), and the spots (se=a reference spot, and sa=an analysis spot) on which either the probe molecules and/or inert standards or the probe molecules specific to the analyte are immobilized. This schematic diagram shows that the tube is provided for containment of a reaction liquid (Lr) in contact with the silicon surface.

(S) and (Cc) are shown in top view in the photograph in FIG. 8, shown prior to gluing of the tube and deposition of the resin.

1.3 Functionalization of the Silicon Surface by Probe and Inert Molecules which are Oligonucleotides 1.3.1 Revealing the Silanols (i) Silanols are first revealed on the silicon nitride chip surface: Agitation for 2 h at room temperature in the solution: NaOH 1 g/water 3 ml/ethanol 99% 4 ml. Copious washing with water. Agitation for 1 h in 0.2 N HCl, then copious rinsing with water. Drying at 80° C. in the stove.

ii) silanization: the plates are immersed at room temperature for 24 hours in 3-aminopropyltriethoxysilane at 10% (vol/vol) in ethanol, under argon. Then drying. Then washing with 99% ethanol, then a second washing with 99% ethanol+ ultrasound. Each washing takes several minutes. Drying. Annealing for 3 hours at 110° C. in the dry.

iii) pre-activation: the plates are immersed in KOH solution (1.5 g KOH in 20 ml water). Incubation for 5 to 10 minutes, at room temperature, with agitation. Then rinsing with pure water.

iv) activation: the plates are immersed in a solution of glutaraldehyde (4 ml of glutaraldehyde in 16 ml of water). Incubation 1 h 30 min at room temperature. Rinsing with pure water. Drying.

1.3.2 Immobilization of the Oligonucleotides

After activation of these $NH_2$ groups by glutaraldehyde, aminated oligonucleotides (ODN hereinafter) can be deposited on the various spots of the chip surface for their attachment, by means of a robot from the company Karl Züss equipped with a pipette from the company Mikrodrop. The diameter of the spots was evaluated at approx. 140 μm.

Preparation of the solutions of oligonucleotides to be deposited: the solutions used each comprise 10 μM of ODN in total (probe+inert) to be deposited on each spot of the reference range of the chip. They contain a mixture of reference probe ODN and inert (non-specific) ODN in proportions 100% reference, 10% reference, 1% reference, 0.1% reference, and 100% non-specific, i.e. a reference range produced with 5 spots or points. These 5 solutions were deposited on 5 lines of spots with the robot from the company Karl Züss, equipped with a piezoelectric pipette from the company Mikrodrop. The spots were deposited with spacing of 200 μm. The distance between lines is approx. 400 μm. Spot diameter is approx. 140 μm.

All the oligonucleotides in this experiment have a length of 22 bases. The sequences used are as follows:

```
Sequence of the probe oligonucleotide
(SEQ ID NO: 1):
5' (H2N)-ATGAACAAGTAGATAAATTAGT-3'

Sequence of the inert oligonucleotide
(SEQ ID NO: 2):
5' (H2N)-CTAAAGGAATAGTGTAAATAAT-3'
```

The —$NH_2$ groups serve for attachment on the aldehydes of the glutaraldehyde used in this example.
(The sequence of the reference target oligonucleotide is described in example 3)

1.4 Hybridization and Labelling

These chips were hybridized with a 15 nM solution of HRP conjugate at 37° C. for 30 minutes, washed, then imaged in the presence of Pierce substrate mixture ("Super ELISA Femto Maximum Sensitivity Kit" ®). The HRP conjugate is an oligonucleotide that is complementary to the probe oligonucleotide, to which the HRP enzyme was coupled (HRP: Horse Radish Peroxidase).

All the hybridizations were carried out, in a humid chamber, at 37° C. for 30 minutes in TE 1×, NaCl 1 M, Triton X-100 0.05%. The volume of hybridization is 200 μl (i.e. a liquid layer approx. 3 mm thick). No agitation. Hybridization is followed by 3 washings of 400 μl in TE 1×, NaCl 1 M, Triton X-100 0.05%, then one washing in TE 1×, NaCl 1 M. TE 1× denotes: Tris 10 mM, EDTA 1 mM, pH 8.

After hybridization and the washings, the chip is mounted on a reading card.

1.5 Determination of the Signals of the Reference Range and Reading

The rinsing medium is removed, then 200 μl of the substrate mixture SuperSignal ELISA Femto Maximum Sensitivity Substrate® (Pierce, #37075) is added.

Image acquisition: 50 images with gain 15 divisor 15 (1.8 images/s), 50 images gain 0 divisor 15 (1.8 images/s). The first image series enables weak signals to be visualized. The second permits visualization of strong signals, which saturate the sensor in the above conditions. The 50 luminescence images are averaged pixel by pixel, as well as the 50 black images. Then the average of the black images is subtracted from the average of the luminescence images. On the resulting image obtained, the average intensity of each spot is taken, and the average value of the background noise around the spot is subtracted from this. The value obtained represents the luminescence signal of the spot.

Figure 3:
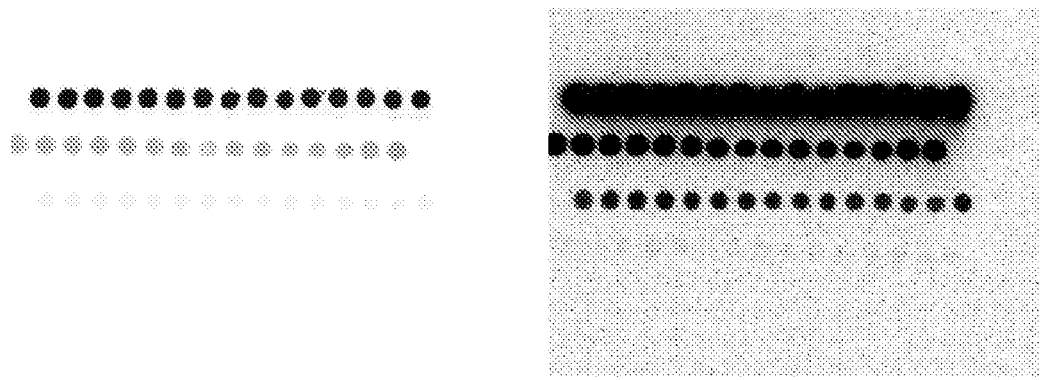
FIG. 3 shows two negatives of images of a reference range on a chip according to the invention with exposure of 560 ms, gain 0 (left) or 16 (right).

In fact, the dynamic range of the sensor (estimated theoretically at 320) is not sufficient to cover the dynamic range of signals generated by biological samples. It was therefore necessary to perform two acquisitions with different settings for gain or exposure. The conditions selected (gain 0/exposure 560 ms, and gain 16/exposure 560 ms) make it possible to obtain a non-saturated image for the strong signals and an image of the weak signals: photographs in FIG. 3, on the left gain 0 and on the right gain 16. In the image on the right, we can clearly distinguish, even before processing the image, four horizontal lines of spots, from top to bottom: 100%, 10%, 1%, 0.1% reference followed by a line of spots not containing any probe reference molecule, but only the inert (non-specific) molecule, which is not visible.

Figure 4:
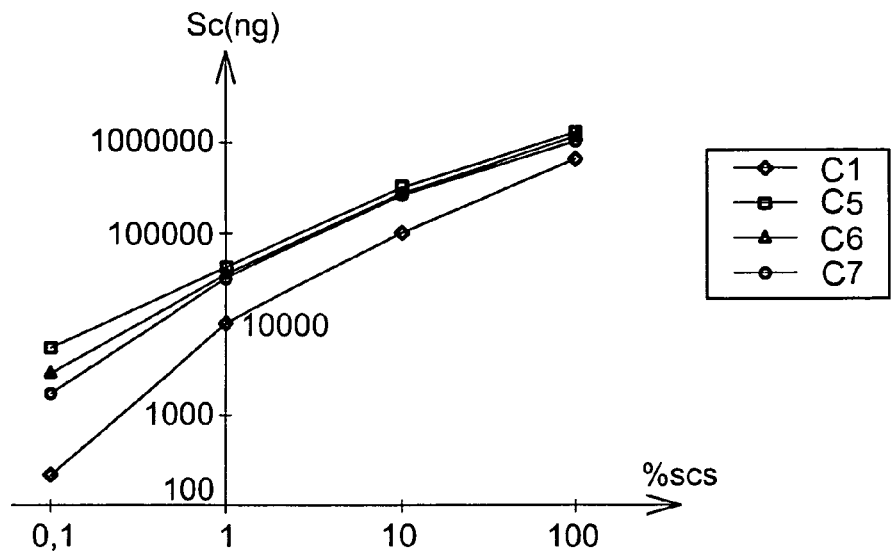
FIG. 4 is a graph showing curves of signals as a function of the proportion of reference oligonucleotide on the capturing spots, for four independent experiments (C1, C5, C6 and C7). These curves constitute reference curves obtained from the reference ranges according to the present invention.

The grey levels (GL) of the spots on the processed images were quantified, then normalized, and the values obtained are shown on the graph in FIG. 4. In FIG. 4, C1, C5, C6 and C7 (C for chip) represent four independent experiments on four different chips according to the present invention. The corrected signal (Sc) (in GL) is shown on the ordinate, and the percentage of probe molecule captured (% SCS) is shown on the abscissa.

It can be seen from this graph that detection by enzyme-coupled hybridization of reference targets makes it possible to distinguish the surface concentrations of each spot of the reference range (here, capture reference probes specific to the reference target) over a useful range of 1000 (from 0.1% to 100%).

This system simulates variation of the surface concentration of spots of captured reference targets. It is therefore possible to detect targets with a range of concentrations, i.e. having a dynamic range of detection, of the order of 1000.

In this example, carried out for purposes of demonstration, the chip was hybridized with an oligonucleotide directly coupled to the HRP enzyme. In real applications, there will certainly be other spots on the chip than just the reference spots. Therefore the chip will be hybridized for example with the sample previously labelled with a hapten, for example biotin. During hybridization, an oligonucleotide complementary to the reference oligonucleotide, and labelled with biotin, will be added to the sample. After hybridization, a streptavidin-HRP conjugate, which will attach itself to the biotins present on the chip, will be incubated. Then development by luminescence will be performed, as described above. This "two-time" method was used in the following example, but with particles as markers, rather than enzymes.

Example 2

Direct Labelling of the Target Reference Molecule with Fluorescent Particles

Figure 7:
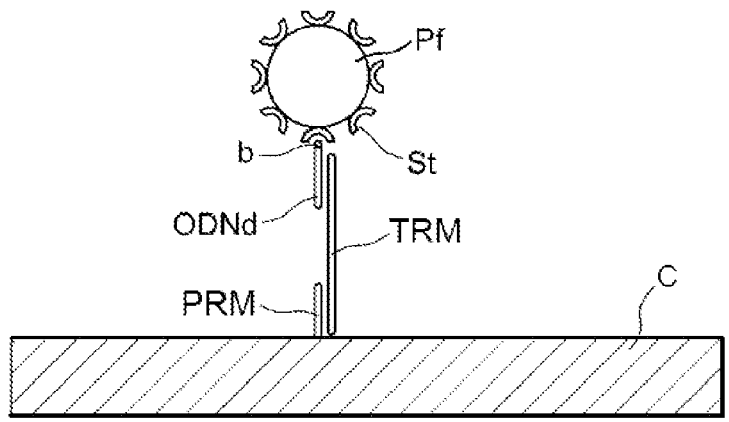
FIG. 7 is a schematic representation of the biochemical mechanism of indirect labelling, with latex particles, of immobilization of the target reference molecule on the reference probe molecule on a chip of the present invention.

In this example, the target reference molecule (TRM) hybridized on the chip (C) is labelled with a hapten, biotin (b), in this case by means of a detection ODN (ODNd). Then a "staining" step takes place, incubating the chip surface with fluorescent particles (Pf) functionalized with streptavidin (St), which will therefore be immobilized on the biotins (b). The sequences are given below. FIG. 7 shows schematically the biochemical mechanism used in this method, on the surface of the chip: a capture ODN is immobilized on the substrate forming the chip and plays the role of the probe reference oligonucleotide (PRM) of the invention; the combination target+detection ODN plays the role of the complementary (target) oligonucleotide (TRM). The capture ODN (probe) is made up of 70 nucleotides. The target is made up of 513 nucleotides. The detection ODN is made up of 16 nucleotides. The sequences are as follows:

```
Sequence of the probe oligonucleotide
(SEQ ID NO: 3):
5'-TCACTATTAT CTTGTATTAC TACTGCCCCT TCACCTTTCC

AGAGGAGCTT TGCTGGTCCT TTCCAAAGTG-3'

Sequence of the inert oligonucleotide
(SEQ ID NO: 4):
5'-ACTGTTACTG ACCTACCATT TGTTACCTAT GCTAAGCTCA

TTGCACCTCT GATTGCCGAG GCCTTTCTTT-3'

Sequence of the target oligonucleotide
(SEQ ID NO: 5):
5'-ACAGCAGTAC AAATGGCAGT ATTCATCCAC AATTTTAAAA

GAAAAGGGGG GATTGGGGGG TACAGTGCAG GGGAAAGAAT

AGTAGACATA ATAGCAACAG ACATACAAAC TAAAGAATTA

CAAAAACCCT TACAAAAATT CAAAATTTTC GGGTTTATTA

CAGGGACAGC AGAAATCCAC TTTGGAAAGG ACCAGCAAAG

CTCCTCTGGA AAGGTGAAGG GGCAGTAGTA ATACAAGATA

ATAGTGACAT AAAAGTAGTG CCAAGAAGAA AAGCAAAGAT

CATTAGGGAT TATGGAAAAC AGATGGCAGG TGATGATTGT

GTGGCAAGTA GACAGGATGA GATTAGAACA TGGAAAAGTT

TAGTAAAACA CCATATGTAT GTTTCAGGGA AAGCTAGGGG

TAGGTTTTAT AGACATCACT ATGAAAGCCC TCATCCAAGA

ATAAGTTCAG AAGTAAATCG AATTCCCGCG GCCATGGCGG

CCGGGAGCAT GCGACGTCGG GCCCAATTCG CCC-3'

Sequence of the detection oligonucleotide (ODNd)
(SEQ ID NO: 6):
5'-TCTGAACTTATTCTT-3'
```

The efficiency of this staining step is still poorly understood, and varies depending on the experimental conditions, the surface chemistry used for fabricating the DNA chip, the fluorescent particles used, etc. Thus, although the particles can be counted individually, it is nevertheless necessary, in the methods of the prior art, to calibrate the measurements to be able to compare the experiments with one another.

Hence the benefit of the present invention for this type of labelling as well, as it makes it possible, advantageously, to dispense with this calibration.

The substrate forming the chip in this example is a microscope slide, 25×75 mm. For all the operations, the microscope slide is immersed in a small beaker containing the required solution. The operations are as follows:

Steps (i) to (iv) of paragraph 1.3.1 of Example 1 above are applied to this substrate. Then:

(1) Immobilization of the aforementioned probe and inert oligonucleotides: Manual deposition, by micropipette, of aminated oligonucleotides at 10 μM, as a 3 μl droplet. The size of the spots is approx. 3 mm. Incubation in a humid chamber overnight at room temperature.

Preparation of the solutions of oligonucleotides to be deposited: the 10 μM mixture of capture ODN deposited contains a mixture of reference and non-specific ODN in proportions 100% reference, 1% reference, 0.2% reference, 0.1% reference, 0.033% and 100% inert (non-specific) molecule (i.e. a reference range produced with 6 points). These 6 solutions were deposited manually.

(2) Post-immobilization treatment. Reduction of the aldehydes still present: water 30 ml/NaBH4 105 mg; incubation 1 h at room temperature, without agitation. Rinsing with water 5 min, then with 5% sodium dodecylsulfate 5 min, then again in pure water 5 min. Drying.

(3) Hybridization of the chip and detection: the chips were hybridized with the aforementioned target molecule of 513 bases (SEQ ID NO:5) at 100 nM for 30 min at room temperature in TE NaCl 1 M Triton 0.05%. Then these chips were hybridized with a 200 nM solution of the detection oligonucleotide at room temperature for 1 hour, then washed. This oligonucleotide is labelled with biotin. Next, the slide was incubated with neutravidin fluorescent particles of 100 nm diameter (Molecular Probes, T8861).

Hybridization: all the hybridizations were carried out at room temperature in TE 1×, NaCl 1 M, Triton X-100 0.05%.

No agitation. Hybridization was followed by 3 washings in TE 1×, NaCl 1 M, Triton X-100 0.05%, then one washing in TE 1×, NaCl 1 M. TE 1× means: Tris 10 mM, EDTA 1 mM, pH 8.

(4) Development and reading: the fluorescent particles were incubated in TE NaCl 1 M, at a concentration of $10^6$ particles per μl for 3 h, at room temperature. The particles have a diameter of 100 nanometers.

(5) Extraction of the numerical results: each spot is imaged in the fluorescence microscope (fluorescein cube). Then the particle density on each spot is counted, either manually, or automatically by means of a Matlab® routine. The results are consistent between these two methods.

Figure 5:
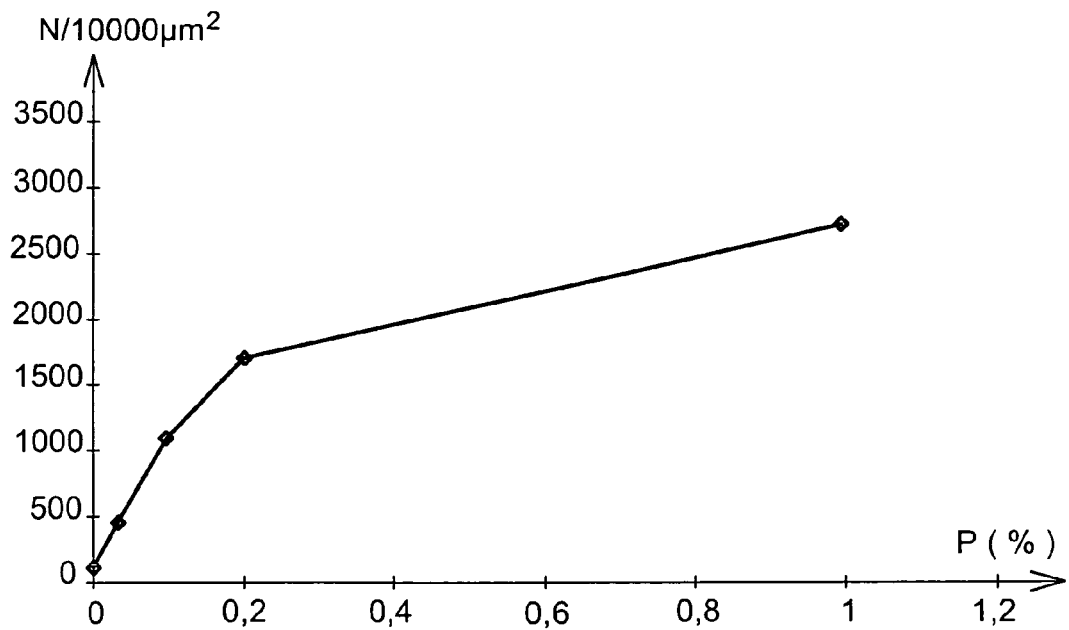
FIG. 5 is a graph summarizing the results of signals determined for each of the spots of a reference range of the present invention with labelling with fluorescent particles.

A usable reference range is certainly obtained. It is shown as the graph in FIG. 5, with the number of particles per 10,000 $\mu m^2$ on the ordinate, and "P (%)" (% PRM/(IM+PRM)) on the abscissa.

When using, instead of the marker mentioned previously, Quantum Dot) fluorescent particles from the company Quantum Dot Corp.®, we can expect to obtain a far better labelling efficiency than that obtained here with fluorescent latices.

Example 3

Analysis of a Sample

We propose, as an example, a simple chip dedicated to initial screening of patients presenting an infection of the upper respiratory tract. The chip is intended more precisely for detecting the presence of the viruses RSV A and RSV B, responsible for bronchiolitis, and the presence of the viruses Influenza A (Inf A) and Influenza B (Inf B), responsible for influenza.

In all cases, they are very polymorphic RNA viruses; the symptoms are relatively similar, and these viruses can be dangerous in infants, in the elderly, and in all immunodepressed patients in general.

The chip used will be of exactly the same technology as in example 1, with functionalization chemistry identical to that of Example 2.

Figure 9:
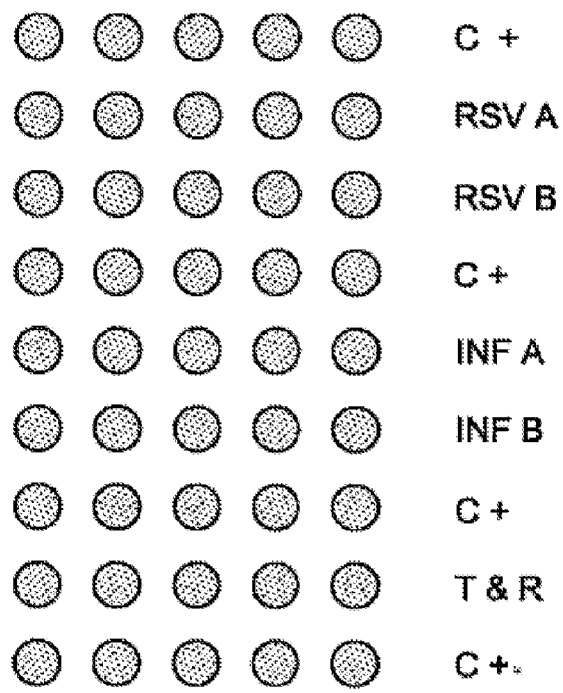
FIG. 9 is a schematic representation of an analysis chip according to the invention for detecting the presence of the viruses RSV A and RSV B responsible for bronchiolitis (RSV: Respiratory Syncytial Virus), and of the viruses Inf A (influenza A) and Inf B (influenza B) responsible for influenza in a patient.

The spots (analysis spots as well as reference range spots) have a diameter of approx. 160 μm, and are arranged with spacing of 300 Him. This chip according to the present invention is shown schematically in FIG. 9. The spots are shown as being circular.

For RSV A, RSV B, Inf A and Inf B, as well as for the "stain" control and development (T & R), it is the same spot repeated five times.

The molecule on the spots for "stain" control and development (T & R) is an oligonucleotide identical to the TRM molecules, already labelled, during production of the oligonucleotides, with biotin.

The positive control (C+) is a reference range in the sense of the invention, in the proportions 100%, 10%, 1%, 0.1%, 0% (from left to right).

The chip will be used in the following way:
a) the biologist purifies the RNAs of the samples according to the methods of the prior art.
b) the biological sample is mixed with the target reference molecule labelled with biotin during production.
c) the sample is labelled with biotin, according to one of the variants of the LDC method which was the object of patent applications filed by BioMérieux in the families of patents corresponding to documents [13], [14], [15] or [16] in the bibliography.
d) the assembly on the chip is incubated (hybridization step), followed by washings, as in example 1.
e) the streptavidin/HRP enzyme conjugate is added, as in example 1. In this step, the conjugate attaches itself to the analytes present on the analysis spots, as well as to the TRM molecules present on the spots of the reference range, as well as to the molecules of the spots for "stain" control and development.
f) development by luminescence is carried out as in example 1.

The sequences of the TRM, inert and PRM oligonucleotides are identical to that of Example 1.

BIBLIOGRAPHY

[1] François GELI, "Puces à ADN et autres systèmes d'analyse", Biofutur n° 206, Le technoscope de Biofutur, pages 1-14, décembre 2000.
[2] Cahill D J, Nordhoff E., "protein arrays and their role in proteomics", Adv. Biochem. Eng. Biotechnol., 2003, 83, 177-187.
[3] Lopez M F, Pluskal M G, "Protein micro- and macroarrays: digitizing the proteome", J. Chromatogr. B Analyt. Technol. Biomed. Life Sci., 2003, 787(1), 19-27.
[4] EP-A-1 119 769.
[5] FR-A-2 784 189.
[6] WO-A-03/023061.
[7] Bar-coding biomolecules with fluorescent nanocrystals, Nature Biotechnology, 2001, 19, 621-622.
[8] FR-A-2 799 281.
[9] FR-A-2 799 282.
[10] Bertrand Jordan, "voyage au pays des puces", médecine/sciences, 1998, 14, 1097-1102.
[11] Troesch A., et al., "Mycobacterium species identification and rifampin resistance testing with high-density DNA probe array", J. Clin. Microbiol., 1999, 37, 49-55.
[12] Christen R. et Mabilat C., "Applications des puces à ADN en bactériologie", Bull. Soc. Fr. Microbiol., 1998, 13, 10-17.
[13] "Procédé de marquage d'un acide ribonucléique et fragments d'ARN marqués ainsi obtenus", FR 98 07870 et ses extensions dans les autres pays (fammille de brevets). Inventeur: A. Laayoun.
[14] "Process for labelling a nucleic acid", EP-A-1 238 116. Inventeurs: A. Banerjee, A. Laayoun, M. Becker, K. Browne, M. Friedenberg, F. Hajjar.
[15] "Process for labelling a nucleic acid and labelled RNA fragments which are obtained thereby", WO-A-01/44506. Inventeurs: A. Laayoun, D. Do, C. Miyada.
[16] "Procédé de marquage et de fragmentation d'ADN", FR n° 01 06039. Inventeurs: J. Lhomme, E. Trevisiol, A. Laayoun, C. Bourget, M. Kotera, C. Tora.

We claim:

1. An analysis chip of at least one analyte present in a liquid sample, said chip comprising:
   (a) at least one analysis spot of said at least one analyte, said analysis spot being arranged on the chip in such a way as to permit the recognition and immobilization specific to the analyte; and
   (b) a reference range (G), said reference range comprising several reference spots each arranged on said chip in a defined manner and independently of one another, each reference spot of this range comprising, immobilized on its surface and in a defined proportion P different for each spot relative to the other reference spots of said range:
      (i) at least one probe reference molecule (PRM) for recognizing and specifically immobilizing a defined target reference molecule (TRM), and
      (ii) at least one inert molecule (IM) incapable of recognizing and attaching to said target reference molecule, the probe reference molecule and the inert molecule both being unable to recognize and immobilize said at least one analyte;
   with $$P = \frac{\text{number of } PRM}{\text{number of } PRM + \text{number of } IM} \text{ and } 0 \leq P \leq 1$$

and, the sum of the number of PRMs+number of IMs being constant from one reference spot to another,
   wherein the probe reference molecule (PRM), the target reference molecule (TRM), and the inert molecule (IM) are oligonucleotides, and do not recognize or immobilize the analyte.

2. A chip according to claim 1, in which the analyte is oligonucleotides or antibodies.

3. A chip according to claim 1, in which the at least one analyte is a nucleic acid, and in which the at least one analysis spot is a spot functionalized by a second nucleic acid complementary to the nucleic acid.

4. A chip according to claim 1, in which the spots of the reference range are disposed on the chip linearly and are arranged as a function of the proportion P of each spot.

5. A diagnostic or analysis kit comprising a chip according to claim 1, wherein the analysis spot comprises probe molecules specific to recognition of the analyte which are oligonucleotides, cDNA, or aptamers.

6. A method of analysis in vitro of at least one analyte in a liquid sample comprising the following steps:
   (a) providing the analysis chip of claim 1;
   (b) immobilizing a first detecting means on the analyte to provide a labeled analyte;
   (c) adding to the sample to be analyzed, comprising the optionally labeled analyte, a target reference molecule (TRM) on which a second detecting means, identical to or different from the first detecting means, has been immobilized, said TRM being capable of recognizing and of binding specifically to the probe reference molecule (PRM) of said analysis chip, said TRM being added to said sample in a sufficient amount to saturate the PRM of the reference range (G) of said chip, thus creating a reference range that is a function of the defined proportion P which is different for each reference spot;
   (d) bringing the sample to be analyzed comprising the labeled analyte and the labeled TRM, into contact with said analysis chip, said analysis chip comprising at least one analysis spot of said at least one analyte in physicochemical conditions such that the analyte binds to its analysis spot on the chip; and the TRM specifically recognizes the PRM and binds to the PRM on the reference spots of the reference range of the analysis chip;
   (e) determining a reference signal emitted by each reference spot of the reference range, said reference signal being a function of the amount of target reference molecule immobilized on the PRM;
   (f) determining an analysis signal emitted by said at least one analysis spot said analysis signal being a function of the amount of labeled analyte immobilized by the analysis spot; and
   (g) comparing the signals determined in steps (e) and (f) step (d) for expressing this analysis signal as a function of P,
   in which the probe reference molecule (PRM), the target reference molecule (TRM), and the inert molecule (IM) are oligonucleotides, and do not recognize or immobilize the analyte.

7. A method for monitoring variations in gene expression in cells or tissues in vitro, which comprises performing the steps of claim 6.

8. A method of genotyping in vitro, which comprises performing the steps of claim 6.

9. A method according to claim 6, in which the at least one analyte is a nucleic acid, and in which the at least one analysis spot is a spot functionalized by a nucleic acid complementary to this nucleic acid.

10. A method according to claim 6, in which the first and the second detecting means involve respectively a first marker and a second marker.

11. A method according to claim 10, in which the first and the second markers are selected independently from the group consisting of fluorescent markers, radioactive markers, enzymatic markers, latex particles, photonic crystals and colloidal gold.

12. A method according to claim 6, in which the determination of the signal of each spot of the reference range and/or of each analysis spot is performed by a method selected from the group consisting of methods of detection by surface plasmon resonance, methods of photothermal detection, ellipsometric techniques and methods of photometric detection.

13. A method according to claim 6, in which the analysis is a detection or a quantitative analysis.

* * * * *

SEQUENCE LISTING

<160> NUMBER OF SEQ ID NOS: 6

<210> SEQ ID NO 1

```
<211> LENGTH: 22
<212> TYPE: DNA
<213> ORGANISM: Artificial Sequence
<220> FEATURE:
<223> OTHER INFORMATION: Oligonucleotide probe

<400> SEQUENCE: 1
atgaacaagt agataaatta gt                                              22

<210> SEQ ID NO 2
<211> LENGTH: 22
<212> TYPE: DNA
<213> ORGANISM: Artificial Sequence
<220> FEATURE:
<223> OTHER INFORMATION: Inert oligonucleotide

<400> SEQUENCE: 2
ctaaaggaat agtgtaaata at                                              22

<210> SEQ ID NO 3
<211> LENGTH: 70
<212> TYPE: DNA
<213> ORGANISM: Artificial Sequence
<220> FEATURE:
<223> OTHER INFORMATION: Oligonucleotide probe

<400> SEQUENCE: 3
tcactattat cttgtattac tactgccccct tcacctttcc agaggagctt tgctggtcct    60
ttccaaagtg                                                            70

<210> SEQ ID NO 4
<211> LENGTH: 70
<212> TYPE: DNA
<213> ORGANISM: Artificial Sequence
<220> FEATURE:
<223> OTHER INFORMATION: Inert oligonucleotide

<400> SEQUENCE: 4
actgttactg acctaccatt tgttacctat gctaagctca ttgcacctct gattgccgag    60
gcctttcttt                                                            70

<210> SEQ ID NO 5
<211> LENGTH: 513
<212> TYPE: DNA
<213> ORGANISM: Artificial Sequence
<220> FEATURE:
<223> OTHER INFORMATION: Target oligonucleotide

<400> SEQUENCE: 5
acagcagtac aaatggcagt attcatccac aattttaaaa gaaaaggggg gattgggggg    60
tacagtgcag gggaaagaat agtagacata atagcaacag acatacaaac taagaattac   120 aaaaaccct tacaaaaatt caaaattttc gggtttatta cagggacagc agaaatccac   180
tttggaaagg accagcaaag ctcctctgga aaggtgaagg ggcagtagta atacaagata   240
atagtgacat aaaagtagtg ccaagaagaa aagcaaagat cattagggat tatggaaaac   300
agatggcagg tgatgattgt gtggcaagta gacaggatga gattagaaca tggaaaagtt   360
tagtaaaaca ccatatgtat gtttcaggga aagctagggg taggttttat agacatcact   420
atgaaagccc tcatccaaga ataagttcag aagtaaatcg aattcccgcg gccatggcgg   480
ccgggagcat gcgacgtcgg gcccaattcg ccc                                513

<210> SEQ ID NO 6
```

```
<211> LENGTH: 16
<212> TYPE: DNA
<213> ORGANISM: Artificial Sequence
<220> FEATURE:
<223> OTHER INFORMATION: Detection oligonucleotide

<400> SEQUENCE: 6
ttctgaactt attctt                                                        16
```